(12) United States Patent
Beatty (10) Patent No.: US 7,688,068 B2
(45) Date of Patent: Mar. 30, 2010

(54) SYSTEM AND METHOD FOR USING PARALLEL IMAGING WITH COMPRESSED SENSING

(75) Inventor: Philip James Beatty, Menlo Park, CA (US)

(73) Assignee: General Electric Company, Schenectady, NY (US)

( * ) Notice: Subject to any disclaimer, the term of this patent is extended or adjusted under 35 U.S.C. 154(b) by 78 days.

(21) Appl. No.: 12/116,067

(22) Filed: May 6, 2008

(65) Prior Publication Data

US 2009/0278539 A1 Nov. 12, 2009

(51) Int. Cl.
*G01V 3/00* (2006.01)
(52) U.S. Cl. ........................... 324/307; 324/309
(58) Field of Classification Search ......... 324/300–322; 600/407–445
See application file for complete search history.

(56) References Cited

U.S. PATENT DOCUMENTS 7,282,917 B1 * 10/2007 Brau et al. .................. 324/318
7,576,536 B2 * 8/2009 Akao et al. ................. 324/307
7,592,808 B1 * 9/2009 King .......................... 324/307
2009/0069664 A1 * 3/2009 Kim et al. ................... 600/410

OTHER PUBLICATIONS

Lustig et al., "Sparse MRI: The Application of Compressed Sensing for Rapid MR Imaging," Magnetic Resonance in Medicine, 58: 1182-1195, 2007.
Lustig et al., "Rapid MR Imaging with Compressed Sensing and Randomly Undersampled 3DFT Trajectories," Proc. 14th Ann. Mtg. ISMRM, 2006.

* cited by examiner

*Primary Examiner*—Brij B Shrivastav
(74) *Attorney, Agent, or Firm*—Ziolkowski Patent Solutions Group, SC (57) ABSTRACT

A system and method for combining parallel imaging and compressed sensing techniques to reconstruct an MR image includes a computer programmed to acquire undersampled MR data for a plurality of k-space locations that is less than an entirety of a k-space grid. The computer is further programmed to synthesize unacquired MR data by way of a parallel imaging technique for a portion of k-space location at which MR data was not acquired and apply a compressed sensing reconstruction technique to generate a reconstructed image from the acquired undersampled MR data and the synthesized unacquired data.

21 Claims, 4 Drawing Sheets

SYSTEM AND METHOD FOR USING PARALLEL IMAGING WITH COMPRESSED SENSING

BACKGROUND OF THE INVENTION

The invention relates generally to magnetic resonance (MR) imaging and, more particularly, to a system and method of combining parallel imaging and compressed sensing techniques to reconstruct an MR image.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received nuclear magnetic resonance (NMR) signals are digitized and processed to reconstruct the image using one of many well known reconstruction techniques.

One technique that has been developed to accelerate MR data acquisition is commonly referred to as "parallel imaging" or "partial parallel imaging". Various parallel imaging methods exist, including Simultaneous Acquisition of Spatial Harmonics (SMASH), Automatic Simultaneous Acquisition of Spatial Harmonics (AUTO-SMASH), Generalized Autocalibrating Partially Parallel Acquisition (GRAPPA), Parallel Magnetic Resonance Imaging with Adaptive Radius in k-space (PARS), Autocalibrating Reconstruction for Cartesian Sampling (ARC), and Anti-aliasing Partially Parallel Encoded Acquisition Reconstruction (APPEAR), among others. In parallel imaging, multiple receive coils acquire data from a region or volume of interest, where the data is undersampled, for example, in a phase-encoding direction so that only a fraction of k-space data is acquired in an image scan. Thus, parallel imaging is used to accelerate data acquisition in one or more dimensions by exploiting the spatial dependence of phased array coil sensitivity. Parallel imaging has not only been shown to be successful in reducing scan time, but also reducing image blurring and geometric distortions. Moreover, parallel imaging can be used to improve spatial or temporal resolution as well as provide increased volumetric coverage.

More recently, another technique for accelerating MR data acquisition known as "compressed sensing" has been developed. Compressed sensing originates from the observation that most medical images have some degree of "compressibility." That is, when transformed into some suitable domain such as a wavelet domain, a substantial number of values can be set to zero (i.e., compressed) with little loss of image quality. In compressed sensing, compressed images are reconstructed using a non-linear reconstruction scheme, such as an L1-norm constraint, wherein the undersampled artifacts in the chosen domain must be sufficiently sparse (or incoherent) to effectively reconstruct the image. Like parallel imaging, compressed sensing has been found to reduce scan time, image blurring, and geometric distortions.

As both parallel imaging and compressed sensing enable accelerated MR data acquisition, there have been previous efforts to combine parallel imaging with compressed sensing. More specifically, efforts have been made to combine the two techniques by including the parallel imaging technique as a data consistency constraint in the compressed sensing reconstruction, thus resulting in a simultaneous implementation of the techniques. However, by incorporating parallel imaging as a data consistency constraint, the computational efficiency of the compressed sensing reconstruction is greatly reduced, thereby negating some of the benefits provided by using the parallel imaging or compressed sensing technique individually.

It would therefore be desirable to have a system and method that combines parallel imaging with compressed sensing that increases computational efficiency, so as to generate a high-quality reconstructed image while also reducing scan time.

BRIEF DESCRIPTION OF THE INVENTION

In accordance with one aspect of the invention, an MR imaging apparatus includes a magnetic resonance imaging system having a plurality of gradient coils positioned about a bore of a magnet, an RF receiver system and an RF switch controlled by a pulse generator that transmits signals to an RF coil assembly to acquire MR images. The system also includes a computer programmed to acquire undersampled MR data for a plurality of k-space locations that is less than an entirety of a k-space grid. The computer is further programmed to synthesize unacquired MR data by way of a parallel imaging technique for a portion of k-space location at which MR data was not acquired and apply a compressed sensing reconstruction technique to generate a reconstructed image from the acquired undersampled MR data and the synthesized unacquired data.

Another aspect of the invention includes a computer-readable storage medium having a computer program stored thereon. The computer program includes instructions which, when executed by a computer, acquire MR data from an object of interest from an RF receiver coil array, the MR data comprising an undersampled MR data set acquired from a plurality of k-space locations that is less than the entirety of a k-space grid, wherein the MR data is acquired in a clustered incoherent pattern within k-space. The program instructions further cause the computer to perform a reconstruction technique to reconstruct an image using the undersampled MR data set.

In accordance with yet another aspect of the invention, a method for generating a magnetic resonance (MR) image includes acquiring undersampled MR data for a plurality of k-space locations, the plurality of k-space locations being arranged to allow for parallel imaging synthesis of unacquired MR data, and applying a parallel imaging technique to synthesize a portion of unacquired MR data. The method further includes combining the acquired undersampled MR data and the synthesized portion of unacquired MR data to generate a resultant MR data set, the resultant MR data set having a desired incoherency, and separately applying a compressed sensing reconstruction technique to the resultant MR data set to obtain a reconstructed image.

Various other features and advantages of the invention will be made apparent from the following detailed description and the drawings.

BRIEF DESCRIPTION OF THE DRAWINGS

The drawings illustrate embodiments presently contemplated for carrying out the invention.

In the drawings.

DETAILED DESCRIPTION OF THE PREFERRED EMBODIMENT

A system and method for reconstructing an MR image by combining parallel imaging and compressed sensing techniques is provided. In this regard, raw k-space data is acquired by way of an undersampling technique such that only a fraction of possible k-space data is acquired. A portion of the unacquired k-space data is synthesized by way of parallel imaging, thus filling-in a greater area in k-space. The remainder of unacquired k-space data is filled-in, and an image is reconstructed, by implementing a compressed sensing technique.

Figure 1:
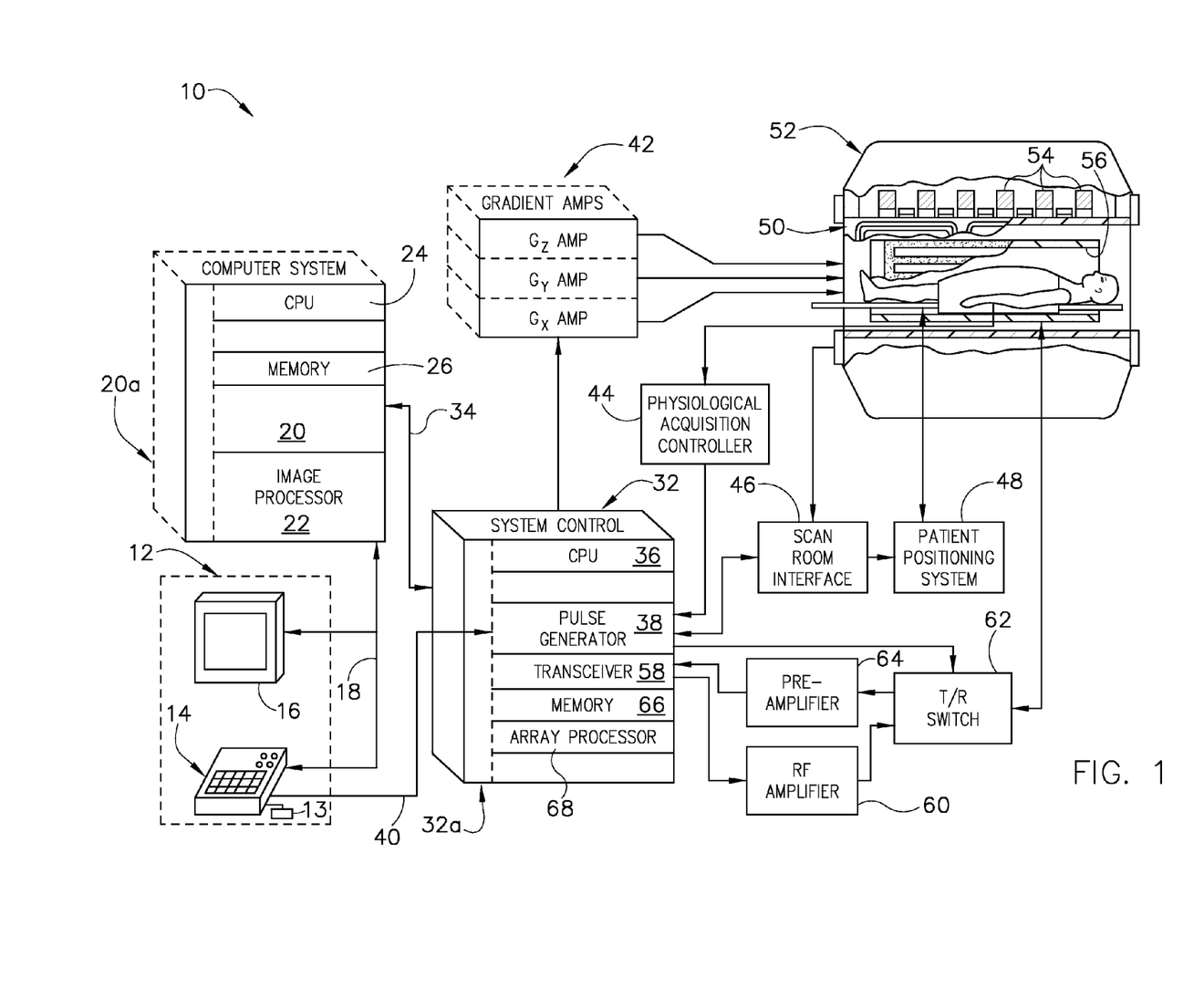
FIG. 1 is a schematic block diagram of an exemplary MR imaging system for use with an embodiment of the invention.

Referring to FIG. 1, the major components of a preferred magnetic resonance imaging (MRI) system 10 incorporating an embodiment of the invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having Gx, Gy, and Gz amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory. In response to commands received from the operator console 12, this image data may be archived in long term storage or it may be further processed by the image processor 22 and conveyed to the operator console 12 and presented on the display 16.

In accordance with the invention, the raw k-space data that is acquired is undersampled so as to acquire only a fraction of possible k-space data. While such undersampling of k-space data reduces the time necessary for performing an image scan, reconstructing an image using only this undersampled k-space data does not remove all artifacts from the image. Therefore, further correction methods are employed to effectively eliminate these artifacts in the final reconstructed image while still reducing image scan time, as will be explained in greater detail herebelow.

Figure 2:
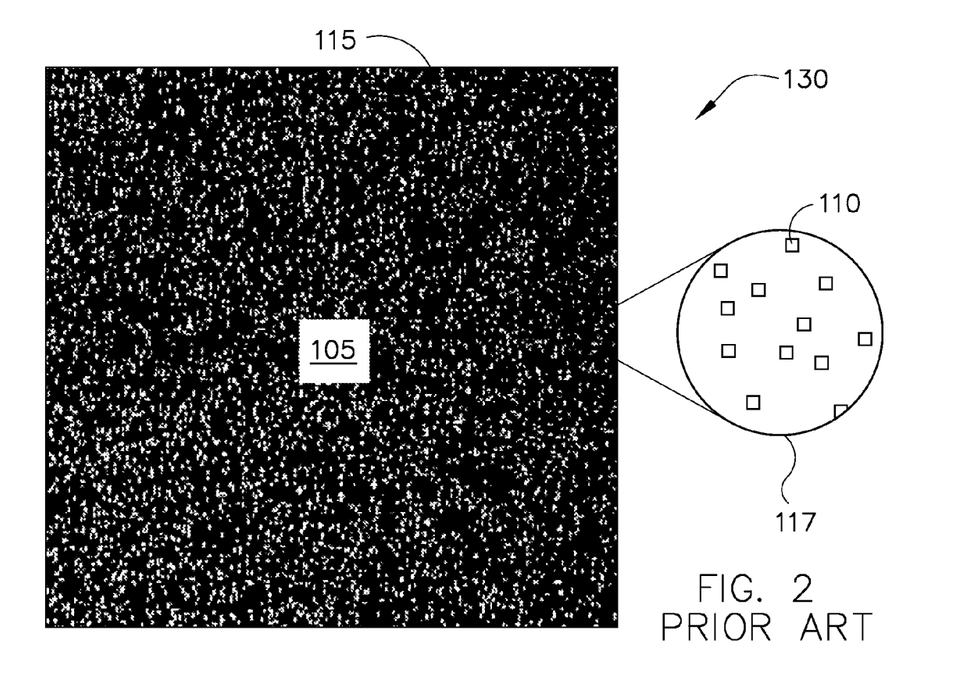
FIG. 2 is a schematic illustration of a k-space data acquisition pattern according to the prior art.

Referring to FIG. 2, an example of a k-space sampling pattern according to the prior art is shown. The k-space sampling pattern 130 comprises a 256×256 data point grid, with an undersampled periphery 115 surrounding a 21×21 fully-sampled center region of k-space 105. This fully-sampled center region 105 of k-space includes low-resolution, full field-of-view (FOV) k-space data having high contrast. It is well-known in MR imaging that a significant contribution to the power spectrum of the acquired signal comes from the central region of k-space, and the center of k-space is a major determinant of image contrast. For this reason, certain reconstruction techniques, such as compressed sensing, require that the center region of k-space be fully-sampled, as undersampling the center region would greatly affect the overall contrast of the image.

As shown in FIG. 2, the peripheral region 115 of k-space is undersampled in a pattern such that a plurality of randomly acquired data points 110 are obtained. Thus, the k-space sampling pattern is described herebelow as a "random sampling pattern". At k-space sampling pattern 130, a random sampling pattern outside of a 21×21 fully-sampled central region is acquired, wherein a total of 5883 data samples are acquired. More or fewer data samples may be acquired, as the amounts used herein are solely for exemplary purposes and are not to be considered limiting to the invention. As blown-out area 117 illustrates, the acquired data points 110 are randomly spaced apart throughout k-space. Due to this significantly random spacing of data points, sampling pattern 130 cannot undergo parallel imaging, as the data points 110 are not sufficiently local to one another to allow for any known parallel imaging technique. Thus, an image reconstructed using k-space sampling pattern 130 exhibits significant artifacts. Therefore, while the use of k-space sampling pattern 130 does speed the data acquisition process by randomly acquiring only 5883 data samples, the technique does not enable high-quality image reconstruction comparable to that of a fully-sampled image.

Figure 3:
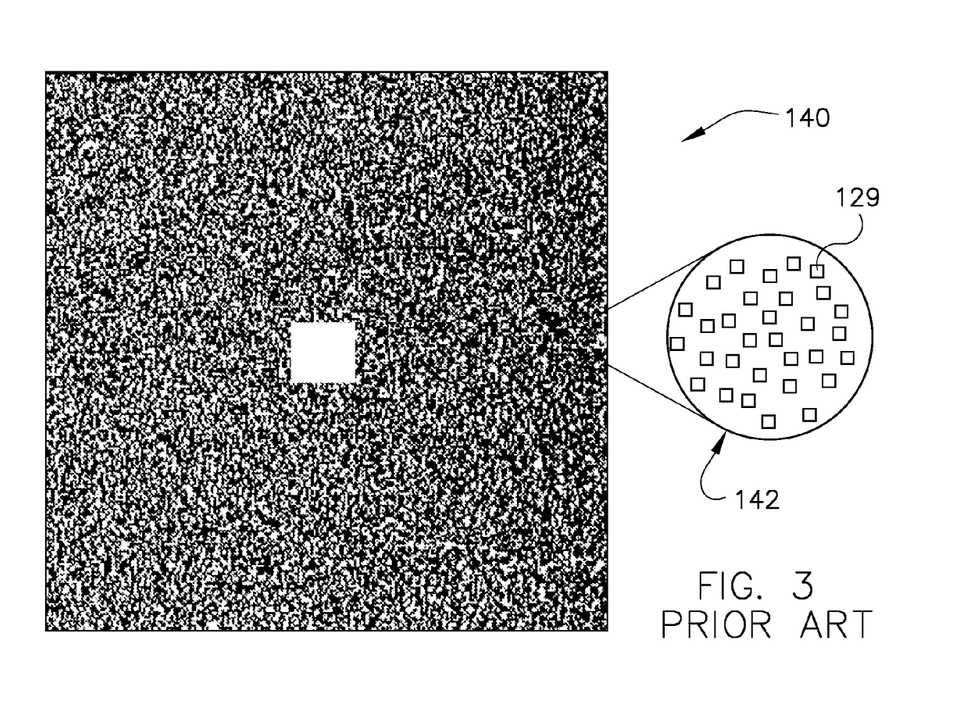
FIG. 3 is a schematic illustration showing a k-space data acquisition pattern according to the prior art.

FIG. 3 shows random k-space sampling pattern 140, which is also indicative of the prior art. Sampling pattern 140 is simply a random k-space sampling pattern wherein 26,726 total data samples are randomly acquired, as opposed to only 5883 data samples in random k-space sampling pattern 130 shown in FIG. 2. As illustrated in blown-out portion 142, data points 129 are randomly acquired throughout k-space, but at a much higher concentration than that which is shown in FIG. 2. Thus, image reconstruction using sampling pattern 140 exhibits few image artifacts, and therefore an image similar to that of a fully-sampled image may be obtained. However, as random k-space sampling pattern 140 contains 26,726 total acquired data points, the amount of acquired data is not significantly reduced in comparison to a fully-sampled image, and thus scan time is not significantly reduced. As will be set forth below, embodiments of the invention provide a reconstructed image having very few artifacts while further reducing overall scan time.

Figure 4:
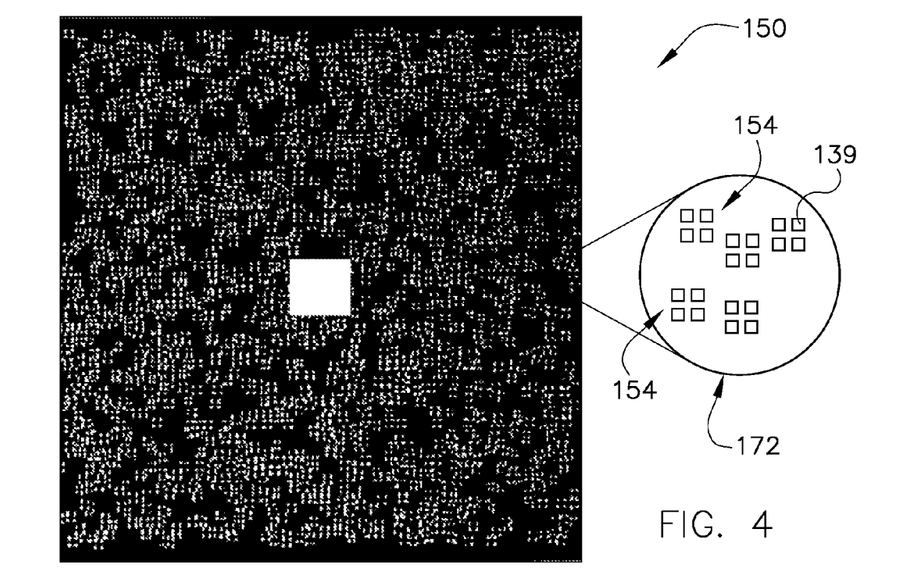
FIG. 4 is a schematic illustration showing a k-space acquisition pattern according to an embodiment of the invention.

Referring now to FIG. 4, the figure represents a "clustered incoherent" k-space sampling pattern 150 according to an embodiment of the invention. As is readily shown, the clustered incoherent sampling pattern outside of a 21×21 fully-sampled central region is acquired having a total of 5883 data samples. Unlike random sampling pattern 130 shown in FIG. 2, however, which also has a total of 5883 data samples acquired, clustered incoherent sampling pattern 150 acquires the data samples in a highly incoherent and highly clustered fashion. Blown-out portion 172 illustrates this highly incoherent yet highly clustered pattern. Any well-known image reconstruction technique can then be used to reconstruct an image using the data samples from clustered incoherent sampling pattern 150. As with FIG. 2 above, however, an image reconstructed using only clustered random sampling pattern 150 may exhibit significant artifacts, as the 5883 data samples alone typically cannot adequately represent a fully-sampled image. However, clustered incoherent sampling pattern 150 is acquired so that in each cluster 154, the space between data points 139 is not more than 1/field-of-view times the parallel imaging acceleration factor. Such spacing enables a parallel imaging technique to be performed using the acquired data points 139 to synthesize additional unacquired data in each cluster 154 so as to fill in some portions of k-space, as will be set forth below with respect to FIG. 5.

Figure 5:
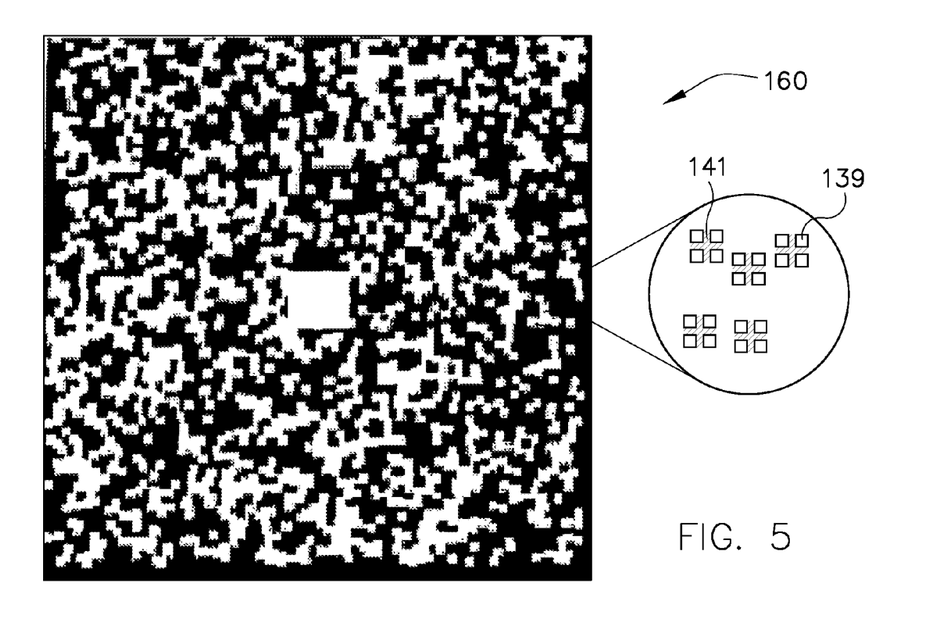
FIG. 5 is a schematic illustration showing a k-space acquisition pattern and synthesis pattern according to an embodiment of the invention.

Referring to FIG. 5, a "synthesized incoherent" k-space sampling pattern 160 is shown. Synthesized incoherent k-space sampling pattern 160 is the outcome of clustered incoherent k-space sampling pattern 150 of FIG. 4 subjected to a parallel imaging technique to synthesize a plurality of unacquired data points 141 local to acquired data points 139. Synthesized incoherent k-space sampling pattern 160 uses the 5883 acquired data samples from clustered incoherent k-space sampling pattern 150 to synthesize additional data points through parallel imaging, providing for a total of 26,726 total data samples. As shown, these 26,726 data samples form a plurality of clustered and incoherent data points. Data points 141 are synthesized using a known parallel imaging method such as GRAPPA, ARC, SMASH, AUTO-SMASH, PARS, and APPEAR. As set forth above, only data that is sufficiently local to the acquired clustered incoherent data points 139 in k-space can be successfully synthesized by parallel imaging. Thus, while typical parallel imaging techniques are able to synthesize a complete data set from a coherent and generally equally spaced apart set of acquired k-space data, the incoherent sampling pattern of data points 139 allows for only a portion of unacquired data to be synthesized. That is, as illustrated in FIG. 5, synthesized data points 141, which are obtained from the application of a parallel imaging method on the acquired clustered incoherent data points 139, do not fill-in a complete data set, but instead create a partially filled grid comprising the incoherent sampling pattern of acquired clustered incoherent data points 139 and the synthesized data points 141 local to the clustered incoherent points. Sampling pattern consists of clusters that are arranged to give incoherent artifacts in the expected-sparse domain (when filled in). Each cluster is composed of data points where the space between data points is not more than the 1/field-of-view times the acceleration factor.

It is further understood that the sampling pattern used to acquire data point clusters 154 is a pattern that undersamples in a domain in which the image to be reconstructed is expected to be sparse. That is, in most complex medical images, the images exhibit transform sparsity, meaning that the image has a sparse representation in terms of spatial finite differences, their wavelet coefficients, or other transforms. A clustered incoherent sampling pattern consists of clusters of acquired data points that are arranged to give incoherent artifacts in the expected-sparse domain. Each cluster is composed of data points where the space between data points is not more than the 1/field-of-view times the acceleration factor, so as to allow for a parallel imaging technique to be performed. Therefore, even though the acquired data point clusters 154 represent only a small amount of possible k-space data, the transform coefficients of the unacquired data points are generally negligible or unimportant, and thus the image can be successfully reconstructed without them.

The synthesized incoherent k-space sampling pattern shown in FIG. 5 is meant to augment a reconstruction method known as compressed sensing. Compressed sensing is an image reconstruction technique originating from the observation that most medical images have some degree of compressibility. For the compressed sensing technique, it is desired that the image have a sparse representation in a known transform domain (such as the wavelet domain) and that the aliasing artifacts due to k-space undersampling be incoherent in that transform domain (i.e., noise-like). In other words, the data sampling pattern is chosen so as to reduce coherency in the sparse domain. This incoherence may be achieved by randomly undersampling the data points, as shown in FIG. 5. The undersampling of data results in aliasing, and when the undersampling is random (as in FIG. 5), the aliasing is incoherent and acts as incoherent interference of the sparse transform coefficients. Therefore, using a non-linear reconstruction scheme, such as an L1-norm constraint, the sparse transform coefficients can be recovered and, consequently, the image itself can be reconstructed.

When applying the compressed sensing technique described above, image reconstruction success (i.e., the clarity of the resulting image) is based on the sparsity of the transform coefficients and that the incoherent interference be small and have random statistics. Thus, in the compressed sensing technique, the random undersampling of data to create an incoherent sampling pattern is of great importance. For this reason, the application of a compressed sensing technique to the synthesized incoherent k-space sampling pattern 160 shown in FIG. 5 creates a high quality image with very few artifacts. Further, while both synthesized incoherent k-space sampling pattern 160 and random k-space sampling pattern 140 shown in FIG. 3 comprise 26,726 data points, sampling pattern 160 only contains 5883 "acquired" data points, while the remaining data points were synthesized using a parallel imaging technique. Thus, the invention not only allows for effective image reconstruction using compressed sensing, but it also reduces scan time by using parallel imaging to synthesize unacquired data using only a small amount of acquired data.

Figure 6:
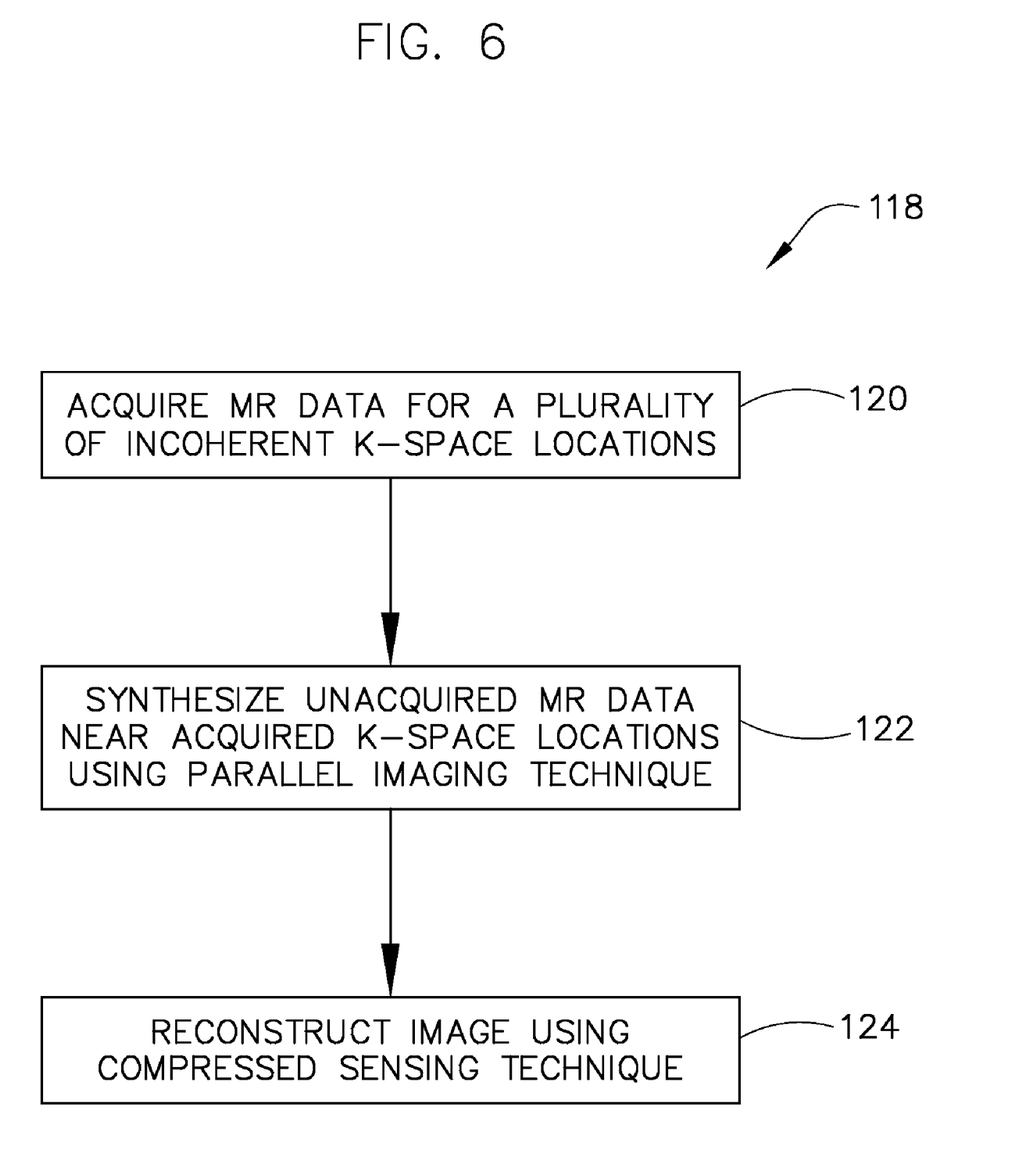
FIG. 6 is a flow diagram according to an embodiment of the invention.

Referring now to FIG. 6, a flow diagram representing a technique 118 for reconstructing an MR image according to an embodiment of the invention is shown. The technique begins at block 120, where undersampled MR data is acquired for a plurality of incoherent k-space locations. As set forth in detail above, the plurality of incoherent k-space locations are, in fact, oriented in a clustered incoherent pattern in which the points are sufficiently local to one another so as to allow for application of a parallel imaging technique thereto. As shown at block 122, unacquired data near the acquired data in k-space is synthesized using any well-known parallel imaging technique. While shown as being performed subsequent to the acquisition of MR data at block 120, it is also envisioned that the synthesis of unacquired data can be performed during clustered incoherent acquisition of the MR data. The synthesized data is unable to fill-in every unacquired data point, but instead creates an augmented data set that includes the originally acquired "clustered incoherent" sampling patterns of k-space space data and the synthesized data obtained via parallel imaging. Finally, at block 124, a compressed sensing technique is applied to reconstruct an image based on the "clustered incoherent" k-space data and the data synthesized via the parallel imaging technique.

The method of image reconstruction shown in FIG. 6 has many advantages over previous work using parallel imaging and compressed sensing. One major advantage is that separating the parallel imaging technique and the compressed sensing technique into two separate "phases" of the reconstruction method enables each technique to be separately tuned and optimized for any given scan sequence. That is, by separately performing parallel imaging, the parallel imaging technique itself can be optimized, without altering the set parameters of the compressed sensing technique. Likewise, the compressed sensing technique can also be independently optimized. Also, as the parallel imaging technique is a separate "phase," the robustness and computational advantages of applying a non-iterative method for parallel imaging (such as GRAPPA and ARC) becomes possible. Further, by applying a parallel imaging "phase" prior to compressed sensing, the size and complexity of the image reconstruction problem presented to the compressed sensing "phase" is greatly reduced, and thus the computational performance of the compressed sensing "phase" is improved. Overall, embodiments of the invention allows for MR scan time to be significantly reduced, as the amount of data actually acquired is minimal, and such a reduction in scan time minimally degrades the image quality.

The steps set forth in FIG. 6 are further operable to be programmed into a computer or computer readable medium. Thus, the invention is capable of being performed automatically through the use of a computer program read by a computer or computer readable medium.

A technical contribution for the disclosed method and apparatus is that it provides for a computer implemented technique that combines separately performed parallel imaging and compressed sensing techniques to reconstruct an MR image while further reducing scan time.

Therefore, according to one embodiment of the invention, an MR imaging apparatus includes a magnetic resonance imaging system having a plurality of gradient coils positioned about a bore of a magnet, an RF receiver system and an RF switch controlled by a pulse generator that transmits signals to an RF coil assembly to acquire MR images. The system also includes a computer programmed to acquire undersampled MR data for a plurality of k-space locations that is less than an entirety of a k-space grid. The computer is further programmed to synthesize unacquired MR data by way of a parallel imaging technique for a portion of k-space location at which MR data was not acquired and apply a compressed sensing reconstruction technique to generate a reconstructed image from the acquired undersampled MR data and the synthesized unacquired data.

Another embodiment of the invention includes a computer-readable storage medium having a computer program stored thereon. The computer program includes instructions which, when executed by a computer, acquire MR data from an object of interest from an RF receiver coil array, the MR data comprising an undersampled MR data set acquired from a plurality of k-space locations that is less than the entirety of a k-space grid, wherein the MR data is acquired in a clustered incoherent pattern within k-space. The program instructions further cause the computer to perform a reconstruction technique to reconstruct an image using the undersampled MR data set.

According to yet another embodiment of the invention, a method for generating a magnetic resonance (MR) image includes acquiring undersampled MR data for a plurality of k-space locations, the plurality of k-space locations being arranged to allow for parallel imaging synthesis of unacquired MR data, and applying a parallel imaging technique to synthesize a portion of unacquired MR data. The method further includes combining the acquired undersampled MR data and the synthesized portion of unacquired MR data to generate a resultant MR data set, the resultant MR data set having a desired incoherency, and separately applying a compressed sensing reconstruction technique to the resultant MR data set to obtain a reconstructed image.

The invention has been described in terms of the preferred embodiment, and it is recognized that equivalents, alternatives, and modifications, aside from those expressly stated, are possible and within the scope of the appending claims. The order and sequence of process or method steps may be varied or re-sequenced according to alternative embodiments.

What is claimed is:

1. An MRI apparatus comprising:
a magnetic resonance imaging (MRI) system having a plurality of gradient coils positioned about a bore of a magnet, and an RF transceiver system and an RF switch controlled by a pulse module to transmit RF signals to an RF coil assembly to acquire MR images; and
a computer comprising a computer readable medium programmed to:
acquire undersampled MR data for a plurality of k-space locations that is less than an entirety of a k-space grid, wherein the acquired undersampled MR data is acquired in a clustered incoherent pattern within k-space;
synthesize unacquired MR data by way of a parallel imaging technique for a portion of k-space locations at which MR data was not acquired; and
apply a compressed sensing reconstruction technique to generate a reconstructed image from the acquired undersampled MR data and the synthesized unacquired MR data.

2. The apparatus of claim 1 wherein the clustered incoherent pattern comprises a Cartesian sampling pattern.

3. The apparatus of claim 1 wherein the computer is further programmed to acquire a center portion of k-space that is fully sampled.

4. The apparatus of claim 1 wherein the computer is further programmed to apply the parallel imaging technique prior to and separate from the compressed sensing technique.

5. The apparatus of claim 1 wherein the parallel imaging technique comprises one of Simultaneous Acquisition of Spatial Harmonics (SMASH), Automatic Simultaneous Acquisition of Spatial Harmonics (AUTO-SMASH), Generalized Autocalibrating Partially Parallel Acquisition (GRAPPA), Parallel Magnetic Resonance Imaging with Adaptive Radius in k-space (PARS), Autocalibrating Reconstruction for Cartesian Sampling (ARC), and Anti-aliasing Partially Parallel Encoded Acquisition Reconstruction (APPEAR).

6. The apparatus of claim 1 wherein the parallel imaging technique and the compressed sensing technique are independently optimized.

7. The apparatus of claim 1 wherein the parallel imaging technique is a non-iterative parallel imaging technique.

8. The apparatus of claim 1 wherein the computer is further programmed to apply the parallel imaging technique concurrent with MR data acquisition.

9. A computer readable storage medium having stored thereon a computer program comprising instructions which when executed by a computer cause the computer to:
acquire MR data from an object of interest from an RF receiver coil array, the MR data comprising an undersampled MR data set acquired at a plurality of k-space locations that is less than the entirety of a k-space grid, wherein the MR data is acquired in a clustered incoherent pattern within k-space; and
perform a reconstruction technique to reconstruct an image using the undersampled MR data set.

10. The computer readable storage medium of claim 9 wherein the reconstruction technique includes performing a parallel imaging technique on the undersampled MR data set to synthesize unacquired MR data local to the acquired MR data; and
performing a compressed sensing reconstruction technique to reconstruct an image using the acquired MR data and synthesized unacquired MR data calculated during the parallel imaging technique.

11. The computer readable storage medium of claim 10 having further instructions to cause the computer to synthesize only unacquired MR data that is sufficiently local to the acquired MR data, the MR data that is sufficiently local to the acquired MR data comprising a portion of the unacquired MR data.

12. The computer readable storage medium of claim 10 having further instructions to cause the computer to separately perform the parallel imaging technique and the compressed sensing technique.

13. The computer readable storage medium of claim 9 having further instructions to cause the computer to acquire a frilly-sampled portion of MR data at a center of k-space.

14. A method of generating a magnetic resonance (MR) image comprising:
acquiring undersampled MR data for a plurality of k-space locations, the plurality of k-space locations being arranged to allow for parallel imaging synthesis of unacquired MR data;
applying a parallel imaging technique to synthesize a portion of unacquired MR data,
combining the acquired undersampled MR data and the synthesized portion of unacquired MR data to generate a resultant MR data set, the resultant MR data set having a desired incoherency; and
separately applying a compressed sensing reconstruction technique to the resultant MR data set to obtain a reconstructed image.

15. The method of claim 14 wherein acquiring undersampled MR data comprises acquiring undersampled MR data in a clustered incoherent pattern of k-space locations within k-space.

16. The method of claim 14 wherein the resultant MR data set comprises MR data for a less than frill k-space grid.

17. The method of claim 14 wherein the parallel imaging technique is a non-iterative parallel imaging technique.

18. The method of claim 14 further comprising independently optimizing each of the parallel imaging technique and the compressed sensing technique.

19. The method of claim 14 further comprising acquiring a fully-sampled portion of MR data at a center of k-space and combining the fully-sampled portion of MR data with the resultant MR data set.

20. An MRI apparatus comprising:
a magnetic resonance imaging (MRI) system having a plurality of gradient coils positioned about a bore of a magnet, and an RF transceiver system and an RF switch controlled by a pulse module to transmit RF signals to an RF coil assembly to acquire MR images; and
a computer comprising a computer readable medium programmed to:
acquire undersampled MR data for a plurality of k-space locations that is less than an entirety of a k-space grid;
acquire a center portion of k-space that is fully sampled;
synthesize unacquired MR data by way of a parallel imaging technique for a portion of k-space locations at which MR data was not acquired;
apply a compressed sensing reconstruction technique to generate a reconstructed image from the acquired undersampled MR data and the synthesized unacquired MR data.

21. An MRI apparatus comprising:
a magnetic resonance imaging (MRI) system having a plurality of gradient coils positioned about a bore of a magnet, and an RF transceiver system and an RF switch controlled by a pulse module to transmit RF signals to an RF coil assembly to acquire MR images; and a computer comprising a computer readable medium programmed to:
  acquire undersampled MR data for a plurality of k-space locations that is less than an entirety of a k-space grid;
  acquire a center portion of k-space that is fully sampled;
  synthesize unacquired MR data by way of a parallel imaging technique for a portion of k-space locations at which MR data was not acquired;
  apply a compressed sensing reconstruction technique to generate a reconstructed image from the acquired undersampled MR data and the synthesized unacquired MR data, wherein the parallel imaging technique is applied prior to and separate from the compressed sensing technique.

* * * * *

UNITED STATES PATENT AND TRADEMARK OFFICE
CERTIFICATE OF CORRECTION

PATENT NO. : 7,688,068 B2
APPLICATION NO. : 12/116067
DATED : March 30, 2010
INVENTOR(S) : Philip James Beatty

It is certified that error appears in the above-identified patent and that said Letters Patent is hereby corrected as shown below:

Col. 10, line 13 (Claim 13), delete "frilly-sampled" and substitute therefore -- fully-sampled --.

Col. 10, line 34 (Claim 16), delete "less than frill" and substitute therefore -- less than full --.

Signed and Sealed this

Eighth Day of June, 2010

David J. Kappos
*Director of the United States Patent and Trademark Office*